United States Patent
Mostowfi et al.

(10) Patent No.: US 8,340,913 B2
(45) Date of Patent: Dec. 25, 2012

(54) PHASE BEHAVIOR ANALYSIS USING A MICROFLUIDIC PLATFORM

(75) Inventors: Farshid Mostowfi, Edmonton (CA); Younes Belahnech, Paris (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 542 days.

(21) Appl. No.: 12/533,305

(22) Filed: Jul. 31, 2009

(65) Prior Publication Data

US 2009/0326827 A1    Dec. 31, 2009

Related U.S. Application Data

(63) Continuation-in-part of application No. PCT/IB2009/050500, filed on Feb. 7, 2009.

(30) Foreign Application Priority Data

Mar. 3, 2008 (CA) .................................. 2623793

(51) Int. Cl.
  *G01N 15/08* (2006.01)
(52) U.S. Cl. ................ 702/12; 702/24; 702/25; 702/49
(58) Field of Classification Search ................ 702/8, 12, 702/45, 50
See application file for complete search history.

(56) References Cited

U.S. PATENT DOCUMENTS

| | | | |
|---|---|---|---|
| 6,543,274 B1 | 4/2003 | Herrmann et al. | |
| 7,351,376 B1 * | 4/2008 | Quake et al. | 422/504 |
| 2001/0041339 A1 * | 11/2001 | Anderson et al. | 435/6 |
| 2002/0050518 A1 * | 5/2002 | Roustaei | 235/454 |
| 2002/0166592 A1 | 11/2002 | Liu et al. | |
| 2004/0007051 A1 * | 1/2004 | Bashir et al. | 73/61.62 |
| 2004/0098202 A1 | 5/2004 | McNeil, III et al. | |
| 2006/0008382 A1 | 1/2006 | Salamitou et al. | |
| 2006/0008913 A1 | 1/2006 | Angelescu et al. | |
| 2007/0054119 A1 * | 3/2007 | Garstecki et al. | 428/402 |
| 2007/0117177 A1 * | 5/2007 | Luo et al. | 435/68.1 |
| 2009/0165876 A1 * | 7/2009 | Atkin et al. | 137/825 |
| 2009/0326279 A1 * | 12/2009 | Tonkovich et al. | 568/487 |
| 2009/0326827 A1 | 12/2009 | Mostowfi et al. | |

OTHER PUBLICATIONS

Chih-Jung Kuo et al, "Bubble Dynamics During Boiling in Enhanced Surface Microchannels", Journal of Microelectromechanical Systems, vol. 15, No. 6, Dec. 2006, pp. 15141527.

D. Jed Harrison et al, "Micromachining a Minaturized Capillary Electrophoresis-Based Chemical Analysis System on a Chip", Science, vol. 261, Aug. 1993, pp. 895-897.

International Search Report and Written Opinion of PCT Application Serial No. PCT/IB2010/053984 dated Feb. 8, 2011.

* cited by examiner

*Primary Examiner* — Jonathan Teixeira Moffat
*Assistant Examiner* — Mischita Henson
(74) *Attorney, Agent, or Firm* — William L. Wang; Wayne I. Kanak

(57) ABSTRACT

Methods and related systems are described for analyzing phase properties in a microfluidic device. A fluid is introduced under pressure into microchannel, and phase states of the fluid are optically detected at a number of locations along the microchannel. Gas and liquid phases of the fluid are distinguished based on a plurality of digital images of the fluid in the microchannel. Bi-level images can be generated based on the digital images, and the fraction of liquid or gas in the fluid can be estimated versus pressure based on the bi-level images. Properties such as bubble point values and/or a phase volume distribution ratio versus pressure for the fluid are can be estimated based on the detected phase states of the fluid.

23 Claims, 17 Drawing Sheets

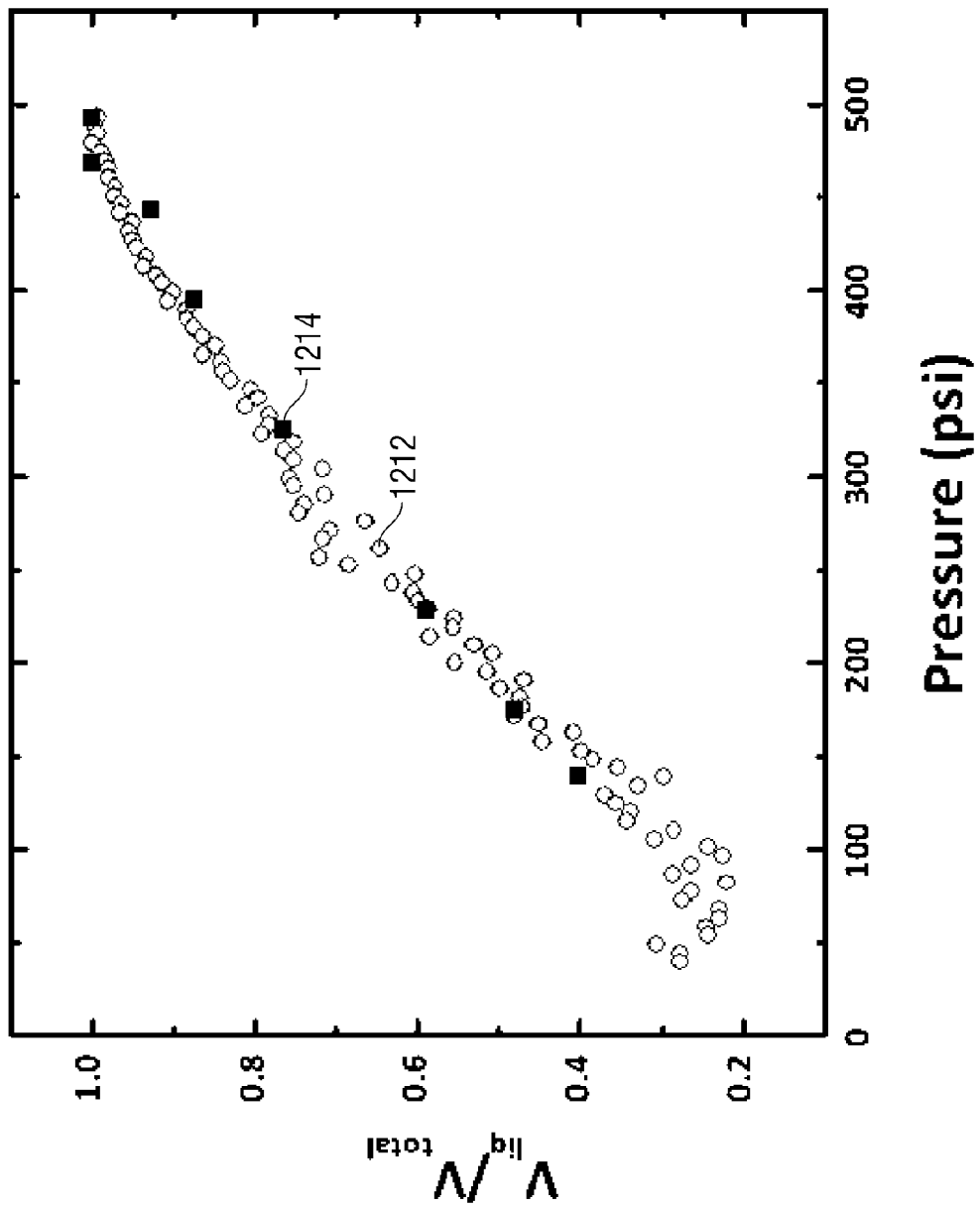

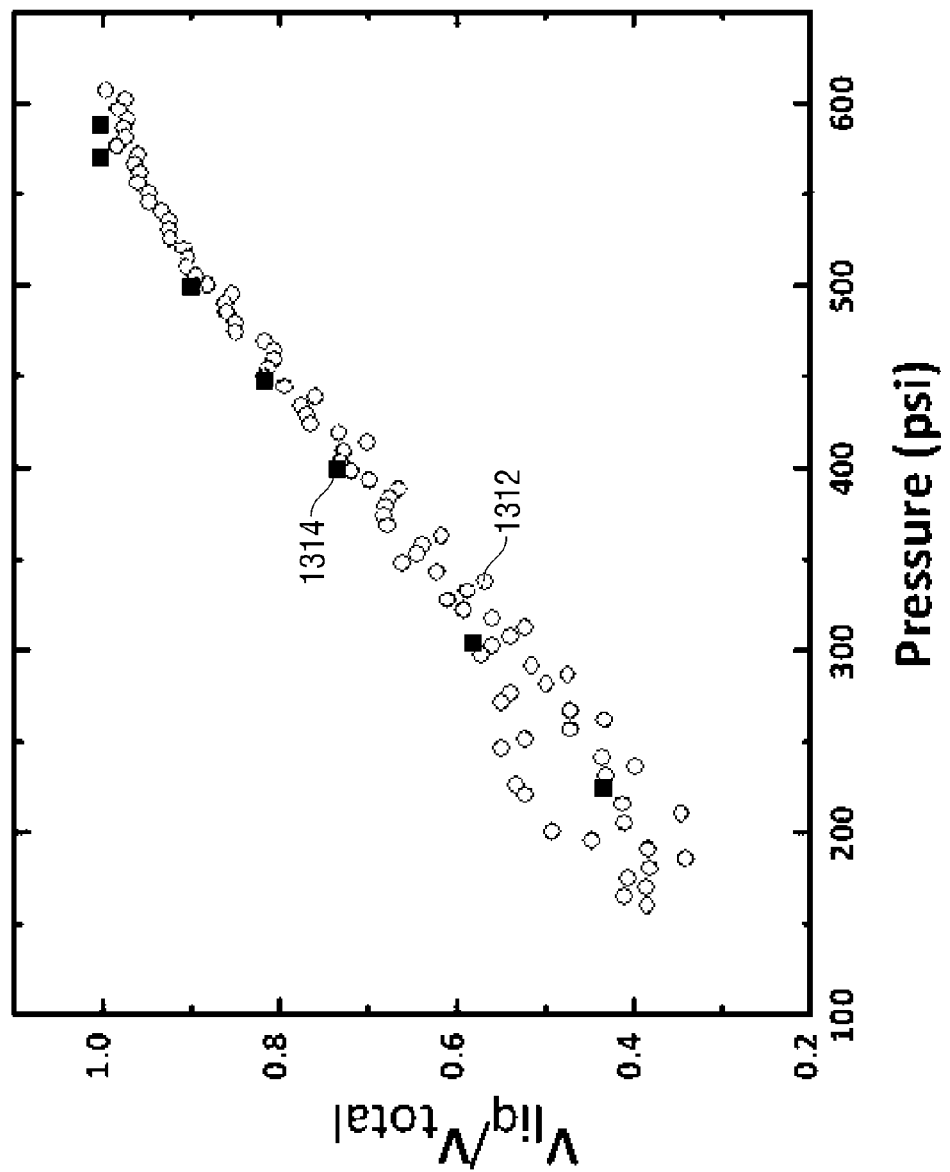

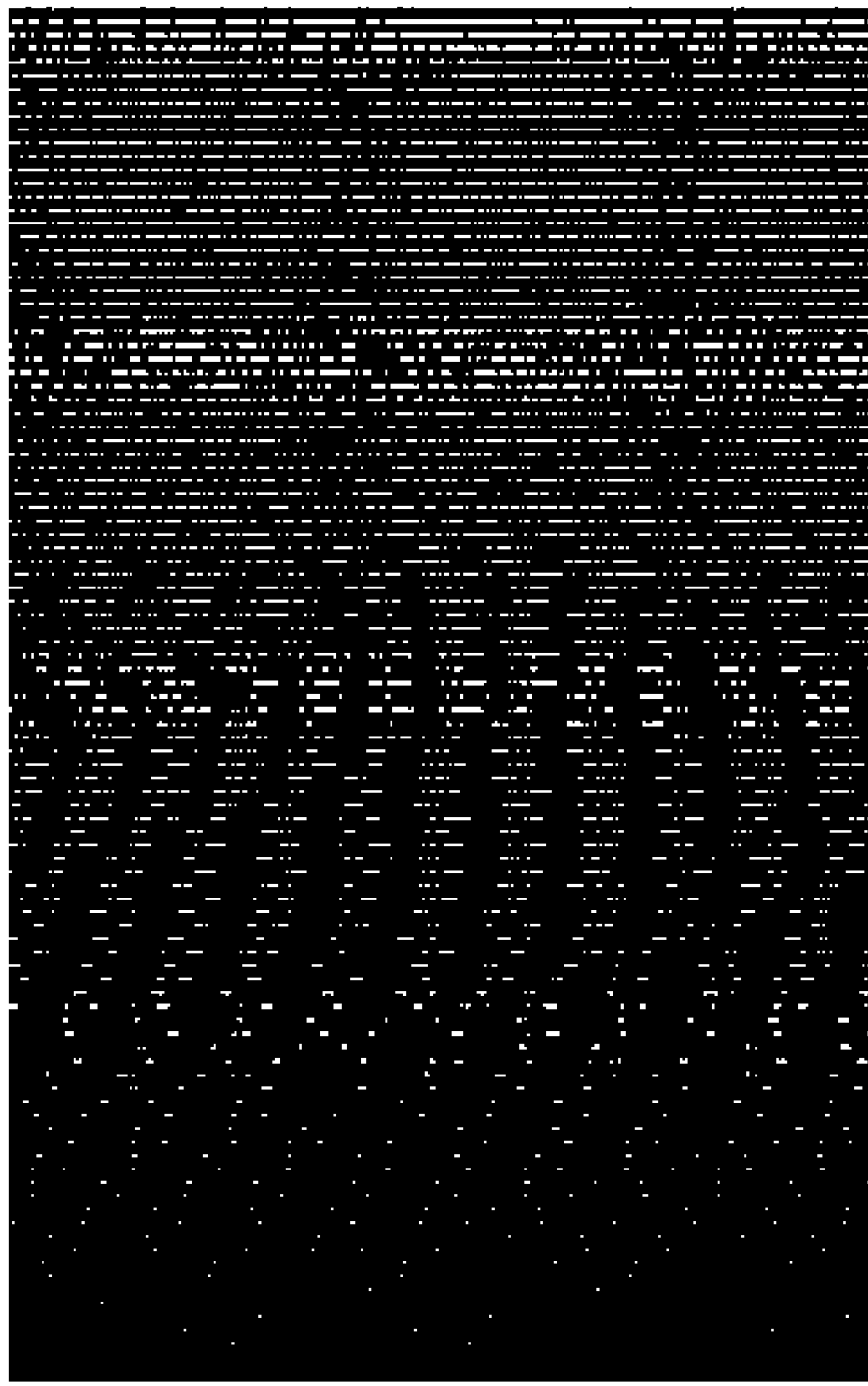

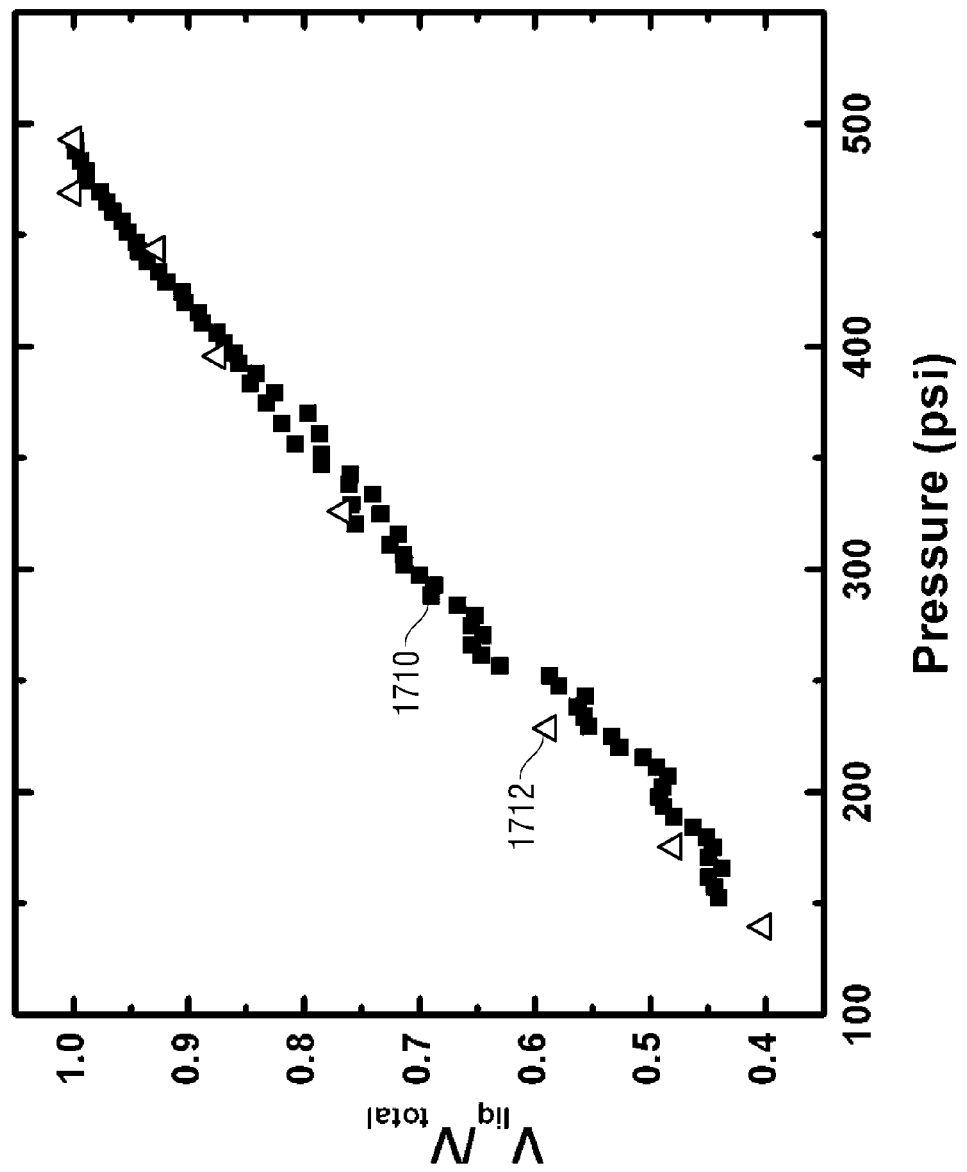

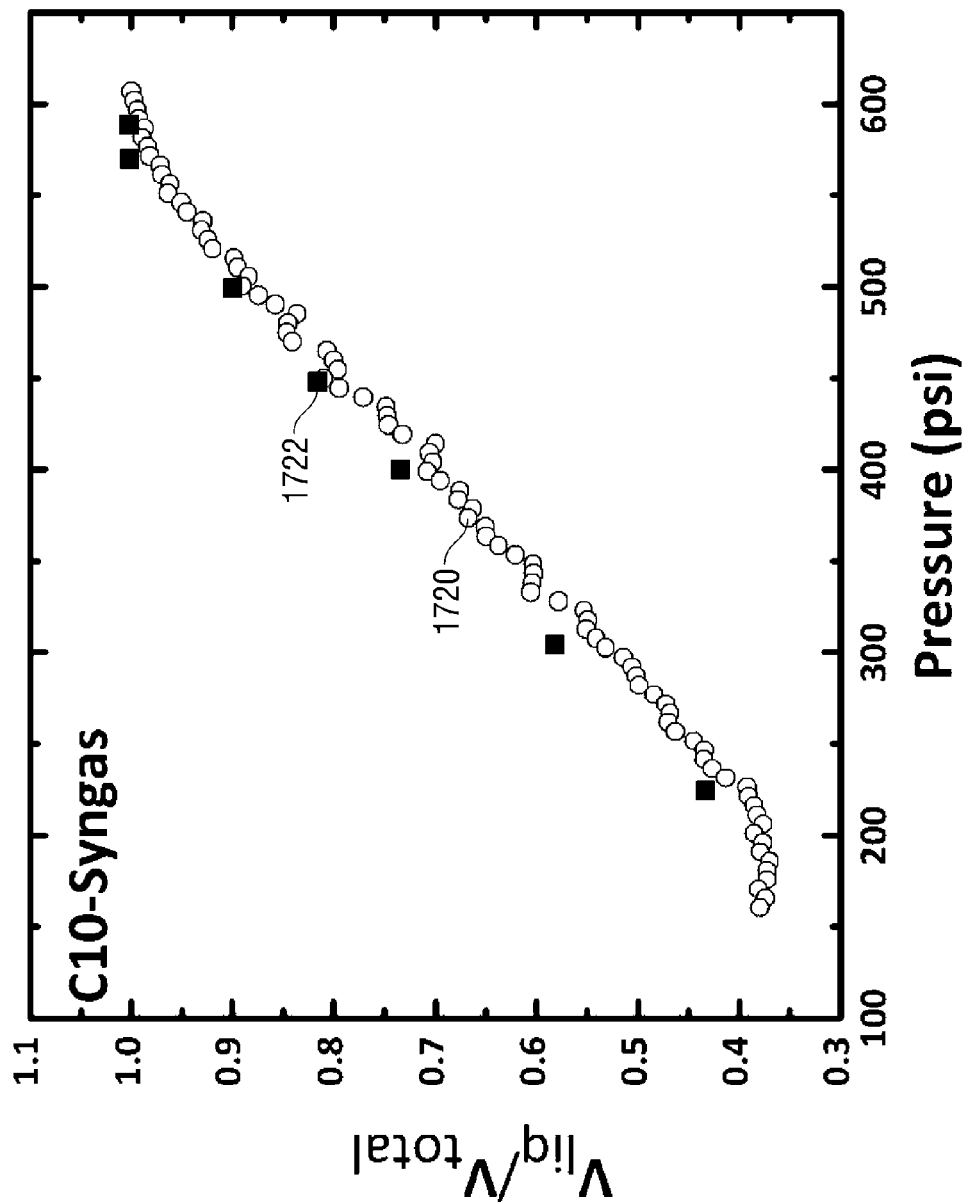

(A - A')

PHASE BEHAVIOR ANALYSIS USING A MICROFLUIDIC PLATFORM

CROSS-REFERENCE TO RELATED APPLICATIONS

This patent application is a continuation-in-part of International Patent Application No. PCT/IB09/50500, filed Feb. 7, 2009, which is incorporated by reference herein.

BACKGROUND OF THE INVENTION

1. Field of the Invention

This patent specification relates to an apparatus and method for measuring thermo-physical properties of a fluid. More particularly, the patent specification relates to an apparatus and method for analyzing phase behavior properties of a reservoir fluid flowing in a microfluidic device.

2. Description of Related Art

The measurement of reservoir fluid properties is a key step in the planning and development of a potential oilfield. It is often desirable to perform such measurements frequently on a producing well to provide an indication of the performance and behavior of the production process. Examples of such measurements are pressure, volume, and temperature measurements, often referred to as "PVT" measurements, which are instrumental in predicting complicated thermo-physical behavior of reservoir fluids. One important use of PVT measurements is the construction of an equation of state describing the state of oil in the reservoir fluid. Other properties of interest that may be determined using PVT measurements include fluid viscosity, density, chemical composition, gas-oil-ratio, and the like. Once a PVT analysis is complete, the equation of state and other parameters can be input into reservoir modeling software to predict the behavior of the oilfield formation.

Conventional PVT measurements are performed using a cylinder containing the reservoir fluid. A piston disposed in the cylinder maintains the desired pressure on the fluid, while the heights of the liquid and gaseous phases are measured using, for example, a cathetometer.

Despite wide application, conventional PVT measurements suffer from several significant limitations. Firstly, a conventional PVT analysis typically requires up to a few weeks to complete. Furthermore, a substantial volume of reservoir fluid, often as much as 4 liters, must be maintained at pressures up to about 1400 kilograms/square centimeter (20,000 pounds/square inch) from the wellsite to the testing laboratory. Shipping and handling such a large sample at these high pressures is costly and poses considerable safety issues.

While there are ways of characterizing properties of reservoir fluid known in the art, considerable shortcomings remain.

BRIEF SUMMARY OF THE INVENTION

According to embodiments, a system for analyzing phase properties in a microfluidic device is provided. The system includes a microchannel adapted to carry a fluid and having an entrance passageway and an exit passageway. A fluid introduction system in fluid communication with the entrance passageway, introduces the fluid under pressure via the entrance passageway. An optical sensing system is adapted and positioned to detect phase states of the fluid at a plurality of locations along the microchannel.

The optical sensing system preferably includes a processing system adapted and programmed to distinguish gas from liquid phases of fluid in the microchannel at a plurality of locations along the microchannel based on a plurality of digital images of the fluid in the microchannel. A plurality of bi-level images are preferably generated based on the digital images of the fluid in the microchannel, and values relating to the fraction of liquid or gas in the fluid is preferably estimated for a plurality of pressures based at least in part on the plurality of bi-level images.

Properties such as bubble point values and/or a phase volume distribution ratio versus pressure for the fluid are preferably estimated based at least in part on the detected phase states of the fluid.

Additionally, according to some embodiments a method for analyzing phase properties in a microfluidic device is provided. A microchannel adapted to carry a fluid is provided that has an entrance passageway and an exit passageway. Fluid is introduced under pressure into the microchannel via the entrance passageway, and phase states of the fluid are optically detected at a plurality of locations along the microchannel.

Further features and advantages of the invention will become more readily apparent from the following detailed description when taken in conjunction with the accompanying drawings.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 12B is a plot showing phase volume distribution versus pressure for a mixture of $C_1$ and $C_{10}$, according to some embodiments;

FIG. 13B is a plot showing phase volume distribution versus pressure for a mixture of a multicomponent gas and $C_{10}$, according to some embodiments;

FIG. 16 shows an example of a matrix of phase states, according to some embodiments;

FIGS. 17A and 17B are plots showing the results of the line scan videos, according to some embodiments;

Figure 1:
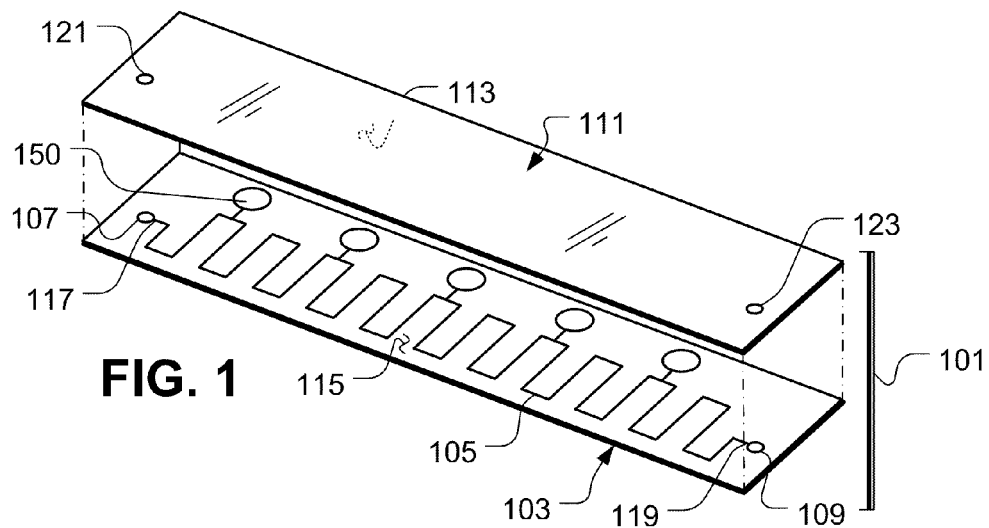
FIG. 1 is a stylized, exploded, perspective view of a first illustrative embodiment of a microfluidic device for measuring thermo-physical properties of a reservoir fluid.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the scope of the invention as defined by the appended claims.

DETAILED DESCRIPTION OF PREFERRED EMBODIMENTS

Illustrative embodiments of the invention are described below. In the interest of clarity, not all features of an actual implementation are described in this specification. It will be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure. Further, like reference numbers and designations in the various drawings indicated like elements.

According to embodiments, techniques for measuring phase behavior of gas-liquid mixtures are provided. The techniques use a microfabricated chip made of a microchannel connected to thin silicon membranes that deform under the fluid pressure. The pressure inside the channel is measured using the membranes as further described in co-pending U.S. patent application Ser. No. 12/533,292, Patent Application Publication No. US 2010/0017135, entitled "PRESSURE MEASUREMENT OF A RESERVOIR FLUID IN A MICROFLUIDIC DEVICE," filed on even date herewith, which is incorporated by reference herein. According to some embodiments, the liquid fraction along the channel is measured by capturing videos of the flow and processing them with a Matlab program. A phase behavior curve is obtained by plotting the liquid fraction against the pressure.

According to embodiments, systems and methods for measuring pressure of a reservoir fluid in a microfluidic device are provided. For the purposes of this disclosure, the term "reservoir fluid" means a fluid stored in or transmitted from a subsurface body of permeable rock. Thus "reservoir fluid" may include, without limitation, hydrocarbon fluids, saline fluids such as saline water, as well as other formation water, and other fluids such as carbon dioxide in a supercritical phase. Moreover, for the purposes of this disclosure, the term "microfluidic" means having a fluid-carrying channel exhibiting a width within a range of a few to hundreds of micrometers, but exhibiting a length that is many times longer than the width of the channel. Similarly the term "microchannel" means a fluid-carrying channel exhibiting a width within a range of a few to hundreds of micrometers. Although many of the microchannels described herein are of rectangular cross section due to the practicalities of fabrication techniques, the cross section of a microchannel can be of any shape, including round, oval, ellipsoid, square, etc.

FIG. 1 depicts a stylized, exploded, perspective view of a microfluidic device 101 for studying phase behavior, according to some embodiments of the invention. In the illustrated embodiment, microfluidic device 101 comprises a first substrate 103 defining a microchannel 105, an entrance well 107 and an exit well 109. Microchannel 105 extends between and is in fluid communication with entrance well 107 and exit well 109. Microchannel 105 forms a serpentine pattern in first substrate 103, thus allowing microchannel 105 to extend a significant length but occupy a relatively small area. According to one embodiment, microchannel 105 exhibits a length of one or more meters, a width of about 100 micrometers, and a depth of about 50 micrometers, although the present invention also contemplates other dimensions for microchannel 105. Microfluidic device 101 further comprises a second substrate 111 having a lower surface 113 that is bonded to an upper surface 115 of first substrate 103. When second substrate 111 is bonded to first substrate 103, microchannel 105 is sealed except for an inlet 117 at entrance well 107 and an outlet 119 at exit well 109. Second substrate 111 defines an entrance passageway 121 and an exit passageway 123 therethrough, which are in fluid communication with entrance well 107 and exit well 109, respectively, of first substrate 103. Also shown in FIG. 1 are a number of cavities such as cavity 150, each connected to the main microchannel 105 using a small side channel. As is explained in further detail below, each cavity such as cavity 150 is partially defined by a deformable membrane that allows for pressure measurement. According to preferred embodiments substrate 103 is fabricated with circular openings and the cavities are defined on the sides by the walls of the openings in substrate 103, on the bottom with the deformable membrane, and on the top by the second substrate 111.

In FIG. 1, first substrate 103 is preferably made of silicon and is approximately 500 micrometers thick, and second substrate 111 is made of glass, such as borosilicate glass, although the present invention contemplates other materials for first substrate 103, as is discussed in greater detail herein. According some preferred embodiments substrate 103 is a conventional silicon on insulator (SOI) wafer. Exemplary borosilicate glasses are manufactured by Schott North America, Inc. of Elmsford, N.Y., USA, and by Corning Incorporated of Corning, N.Y., USA.

In operation, pressurized reservoir fluid is urged through entrance passageway 121, entrance well 107, and inlet 117 into microchannel 105. The reservoir fluid exits microchannel 105 through outlet 119, exit well 109, and exit passageway 123. Microchannel 105 provides substantial resistance to the flow of reservoir fluid therethrough because microchannel 105 is very small in cross-section in relation to the length of microchannel 105. When fluid flow is established between inlet 117 and outlet 119 of microchannel 105, the pressure of the reservoir fluid within microchannel 105 drops from an input pressure, e.g., reservoir pressure, at inlet 117 to an output pressure, e.g., atmospheric pressure, at outlet 119. The flow rate is a function of the overall pressure drop between inlet 117 and outlet 119, and viscosity. Fluid flow through microchannel 105 is laminar and, thus the pressure drop between inlet 117 and outlet 119 is linear when the reservoir fluid exhibits single-phase flow. For further details of microfluidic devices and method for measuring thermo-physical properties of reservoir fluid, see e.g. International Patent Application No. PCT/IB09/50500, filed Feb. 7, 2009, which is incorporated by reference herein. Once the flow is established, the membrane in each cavity, such as cavity 150, deforms due to the fluid pressure and the deformation can be optically detected, as is described more fully in co-pending U.S. patent application Ser. No. 12/533,292, entitled "PRESSURE MEASUREMENT OF A RESERVOIR FLUID IN A MICROFLUIDIC DEVICE", filed on even date herewith.

Figure 2:
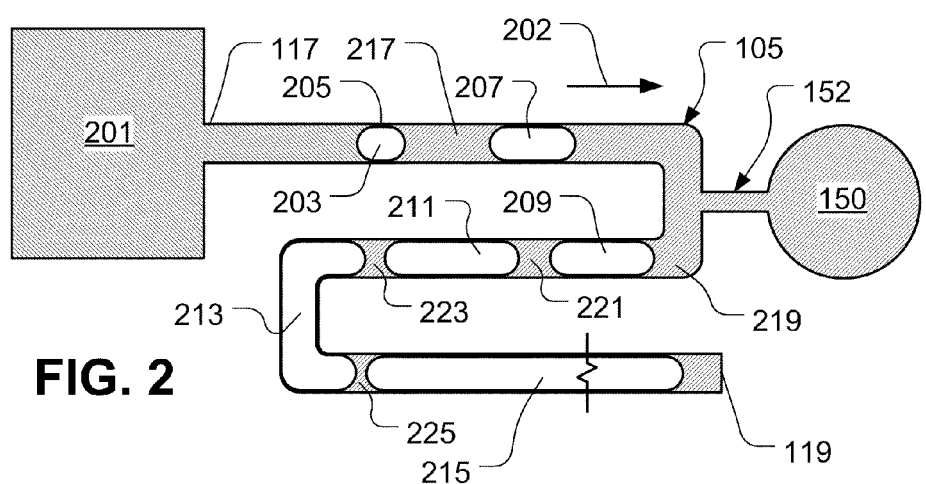
FIG. 2 is a stylized, schematic representation of a reaction of reservoir fluid as the reservoir fluid flows through the microfluidic device of FIG. 1.

FIG. 2 provides a stylized, schematic representation of the reaction of reservoir fluid 201 as the reservoir fluid flows through microchannel 105 in a direction generally corresponding to arrow 202, according to some embodiments. When the reservoir fluid enters inlet 117 of microchannel 105, the reservoir fluid is at a pressure above the "bubble point pressure" of the reservoir fluid. The bubble point pressure of a fluid is the pressure at or below which the fluid begins to boil, i.e., bubble, at a given temperature. When the reservoir fluid exits outlet 119 of microchannel 105, the reservoir fluid is at a pressure below the bubble point pressure of the reservoir fluid. Thus, a "first" bubble 203 forms in the reservoir fluid at some location, e.g., at 205 in FIG. 2, within microchannel 105 where the reservoir fluid is at the bubble point pressure. Downstream of location 205, multi-phase flow, e.g., gas and liquid flow, of reservoir fluid 201 occurs in microchannel 105. Previously-formed bubbles, e.g. bubbles 207, 209, 211, 213, 215, and the like, grow in size as reservoir fluid 201 flows within microchannel 105 beyond the location corresponding to the formation of the first bubble due to decreased pressure in this portion of microchannel 105 and more evaporation of the lighter components of reservoir fluid 201. The bubbles are separated by slugs of liquid, such as slugs 217, 219, 221, 223, 225, and the like. Expansion of the bubbles, such as bubbles 207, 209, 211, 213, 215, results in an increased flow velocity of the bubbles and liquid slugs, such as slugs 217, 219, 221, 223, 225, within microchannel 105. The mass flow rate of reservoir fluid 201 is substantially constant along microchannel 105; however, the volume flow rate of reservoir fluid 201 increases as reservoir fluid flows along microchannel 105. The reservoir fluid also enters cavity 150 through small channel 152. According to some embodiments the width of small side channel 152 is approximately 50 micrometers, or about half of the width of microchannel 105, and is about 50 micrometers deep.

Figure 3:
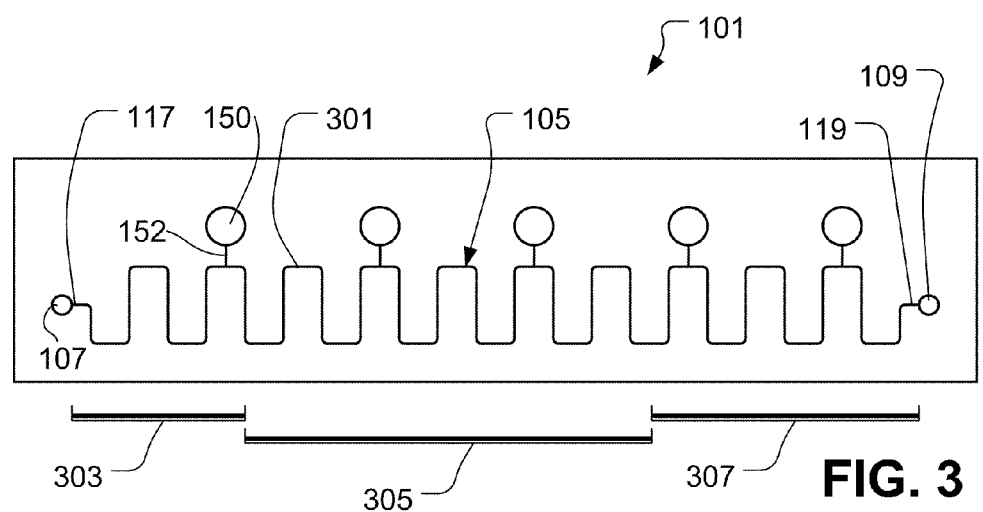
FIG. 3 is a top, plan view of the microfluidic device of FIG. 1 depicting three reservoir fluid flow regimes.

Thermo-physical properties of the reservoir fluid, such as reservoir fluid 201 of FIG. 2, for example gas-oil-ratio, phase envelope, and equation of state, can be determined by measuring the size and concentration of bubbles within microchannel 105. Referring now to FIG. 3, the flow of the reservoir fluid through microchannel 105 is depicted in three regimes. A first bubble, such as first bubble 203 of FIG. 2, is formed at 301 along microchannel 105. From inlet 117 of microchannel 105 to location 301 of the first bubble, indicated in FIG. 3 as a first region 303, the pressure of the reservoir fluid is above the bubble point. No bubbles are observed within first region 303. In first region 303, the flow of the reservoir fluid is laminar due to a low Reynolds number and the pressure drops linearly therein. Once bubbles are formed, the bubbles move along within microchannel 105 toward outlet 119 and the volumes of the bubbles increases. In a second region 305, the void fraction, i.e., the volume of gas to total volume, of the reservoir fluid is less than one. In a third region 307, the flow of the reservoir fluid is dominated by high-speed gas flow. The gas bubbles are separated by small droplets of liquid, such as water. The pressure of the reservoir fluid within third region 307 decreases rapidly. Gas bubbles flow within second region 305 at a slower rate than in third region 307, where they are often nearly impossible to follow with the naked eye.

Figure 4:
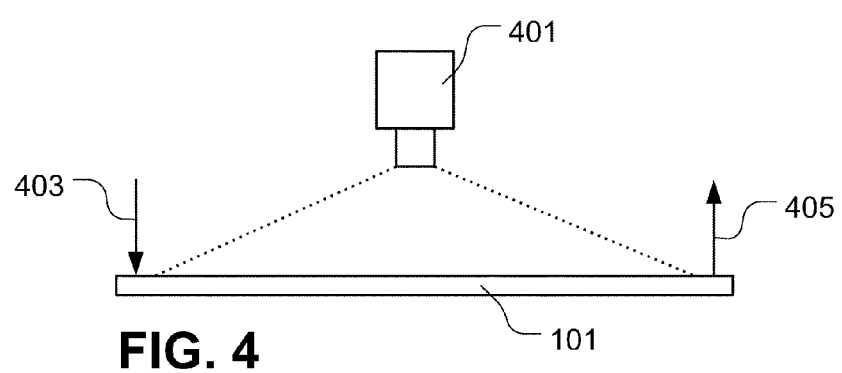
FIG. 4 is a stylized, side, elevational view of a reservoir fluid measurement system, including the microfluidic device of FIG. 1 and a camera for generating images of the microfluidic device in use.

Once a stabilized flow of reservoir fluid is established in microchannel 105, a camera 401 is used to capture snapshots of the flow, as shown in FIG. 4. Note that the flow of reservoir fluid into inlet 117 (shown in FIGS. 1 and 3) is represented by an arrow 403 and that the flow of reservoir fluid from outlet 119 (shown in FIGS. 1 and 3) is represented by an arrow 405. In one embodiment, camera 401 is a charge-coupled device (CCD) type camera. The images produced by camera 401 are processed using image analysis software, such as ImageJ 1.38x, available from the United States National Institutes of Health, of Bethesda, Md., USA, and ProAnalyst, available from Xcitex, Inc. of Cambridge, Mass., USA, to measure the size and concentration of the bubbles in the reservoir fluid disposed in microchannel 105. Using this technique, many thermo-physical properties of the reservoir fluid, such as gas-oil-ratio, phase envelope, and equation of state, can be determined.

Figure 5:
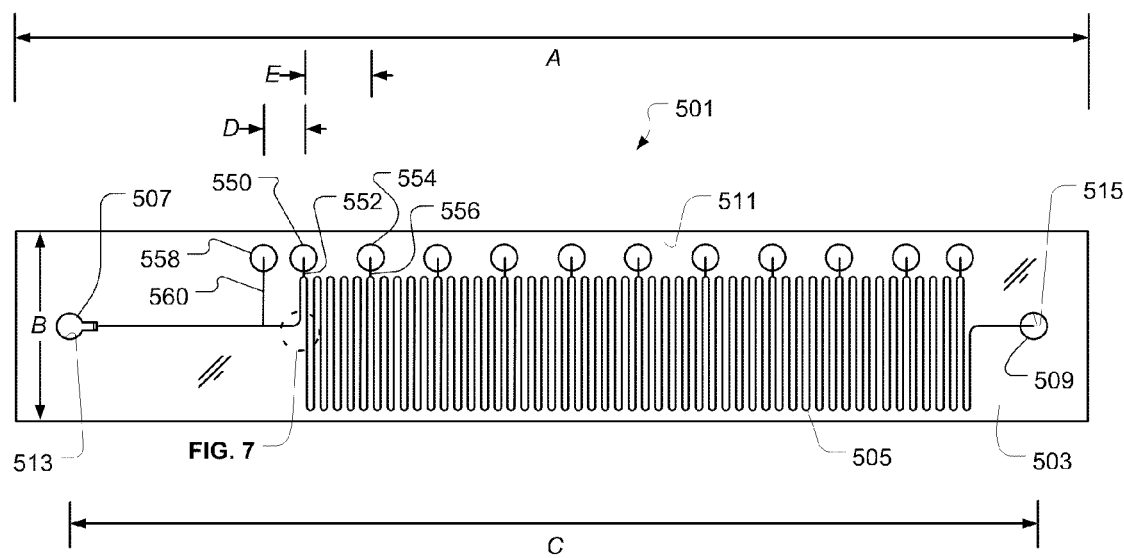
FIG. 5 is a top, plan view of a second illustrative embodiment of a microfluidic device for measuring thermo-physical properties of a reservoir fluid.
Figure 6:
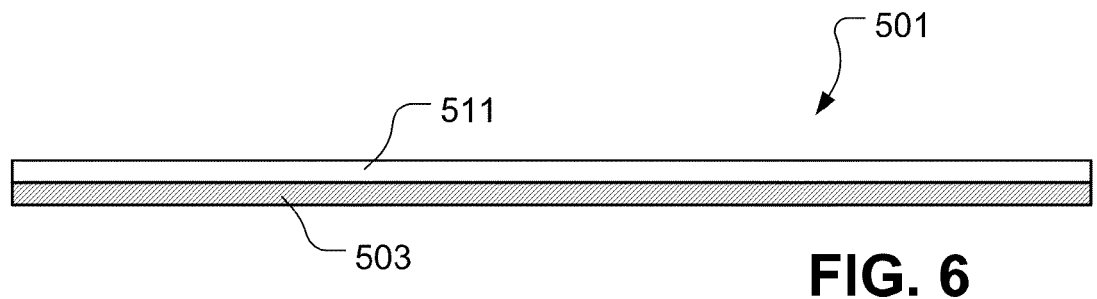
FIG. 6 is a side, elevational view of the microfluidic device of FIG. 5.

FIGS. 5 and 6 depict a microfluidic device 501, according to some embodiments. As in microfluidic device 101 of FIG. 1, microfluidic device 501 comprises a first substrate 503 defining a microchannel 505, an entrance well 507, and an exit well 509. Microchannel 505 extends between and is in fluid communication with entrance well 507 and exit well 509. In the illustrated embodiment, first substrate 503 is made from silicon; however, first substrate 503 may be made from glass. Microchannel 505, entrance well 507, and exit well 509 are, in one embodiment, first patterned onto first substrate 503 using a photolithography technique and then etched into first substrate 503 using a deep reactive ion etching technique. As in the first embodiment shown in FIG. 1, in a preferred embodiment, microchannel 505 exhibits a length of one or more meters, a width of about 100 micrometers, and a depth of about 50 micrometers, although the present invention also contemplates other dimensions for microchannel 505. A number small side channels, such as side channels 552 and 556 lead from the main microchannel 505 to circular cavities such as cavities 550 and 554. Also shown in a side channel 560 that leads to cavity 558. According to some embodiments, twelve cavities are spaced out along the length of microchannel 505 and each of the cavities are about 2 mm in diameter, although the present invention also contemplates other numbers of cavities and diameters for each cavity. Each cavity is partially defined by a flexible membrane on the under side of the device 501. The membranes deform under the local static pressure. The deformation is measured using a Confocal PolyChromatic Sensor (CCS), and after calibration, gives the pressure value inside the channel.

Microfluidic device 501 further comprises a second substrate 511 defining an entrance passageway 513 and an exit passageway 515 in fluid communication with entrance well 507 and exit well 509. Second substrate 511 is made from glass, as discussed herein concerning second substrate 111 (shown in FIG. 1). By making the front of the device 501 transparent, observation of the flow and video capturing of the flow inside the microchannel 505 is provided. In one embodiment, entrance passageway 513 and exit passageway 515 are generated in second substrate 511 using a water jet or abrasive water jet technique. First substrate 503 and second substrate 511 are preferably fused using an anodic bonding method after careful cleaning of the bonding surfaces of substrates 503 and 511.

The present invention contemplates microfluidic device 501 having any suitable size and/or shape needed for a particular implementation. In one embodiment, microfluidic device 501 exhibits an overall length A of about 80 millimeters and an overall width B of about 15 millimeters. In such an embodiment, passageways 513 and 515 are spaced apart a distance C of about 72 millimeters, cavities 558 and 550 are spaced apart a distance D of about 3 millimeters, and cavities along the serpentine section of microchannel 505, such as cavities 550 and 554 are spaced apart by a distance E of about 5 millimeters. It should be noted that microfluidic device 101 may also exhibit dimensions corresponding to microfluidic device 501. However, the scope of the present invention is not so limited.

Figure 7:
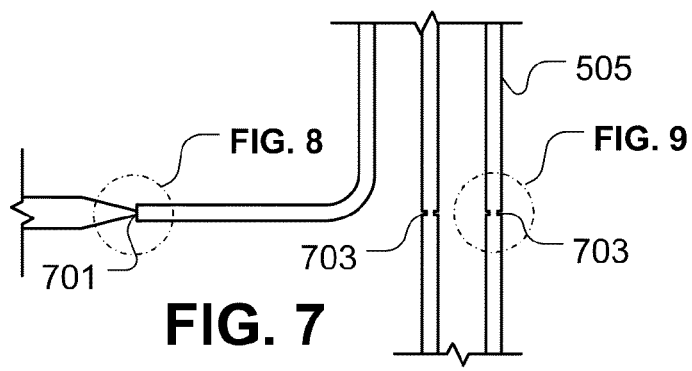
FIGS. 7-9 depict exemplary microchannel constrictions of the microfluidic device of FIG. 5.
Figure 8:
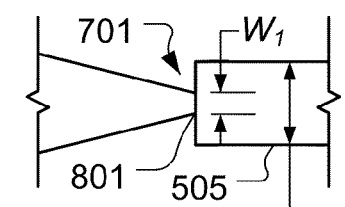
Figure 9:
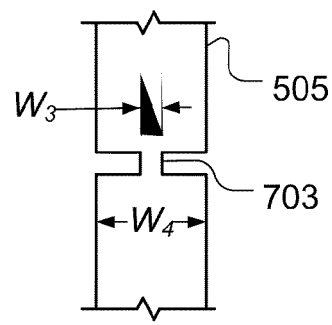

Referring to FIG. 7, one or more portions of microchannel 505 include zones of reduced cross-sectional area to induce the formation of bubble nuclei in the reservoir fluid. For example, as shown in FIGS. 7 and 8, a micro-venturi 701 is incorporated into an inlet of microchannel 505. Micro-venturi 701 includes a nozzle opening 801 having a width $W_1$, which is smaller than a width $W_2$ of microchannel 505. The contraction provided by micro-venturi 701 causes a substantial pressure drop in the reservoir fluid at nozzle opening 801 along with an increased velocity of reservoir fluid flow. The combined effect of the pressure drop and the increased velocity induces formation of bubble nuclei in the reservoir fluid. Preferably, microchannel 505 further includes one or more additional constrictions 703, as shown in FIGS. 7 and 9. Constrictions 703 exhibit widths $W_3$, which are smaller than a width $W_4$ of microchannel 505. Preferably, width $W_1$ of nozzle opening 801 and widths $W_3$ of constrictions 703 are about 20 micrometers, whereas the preferred width $W_2$ and $W_4$ of microchannel 505 is 100 micrometers. These restrictions increase the velocity of the reservoir fluid by up to about 500 percent.

Figure 10:
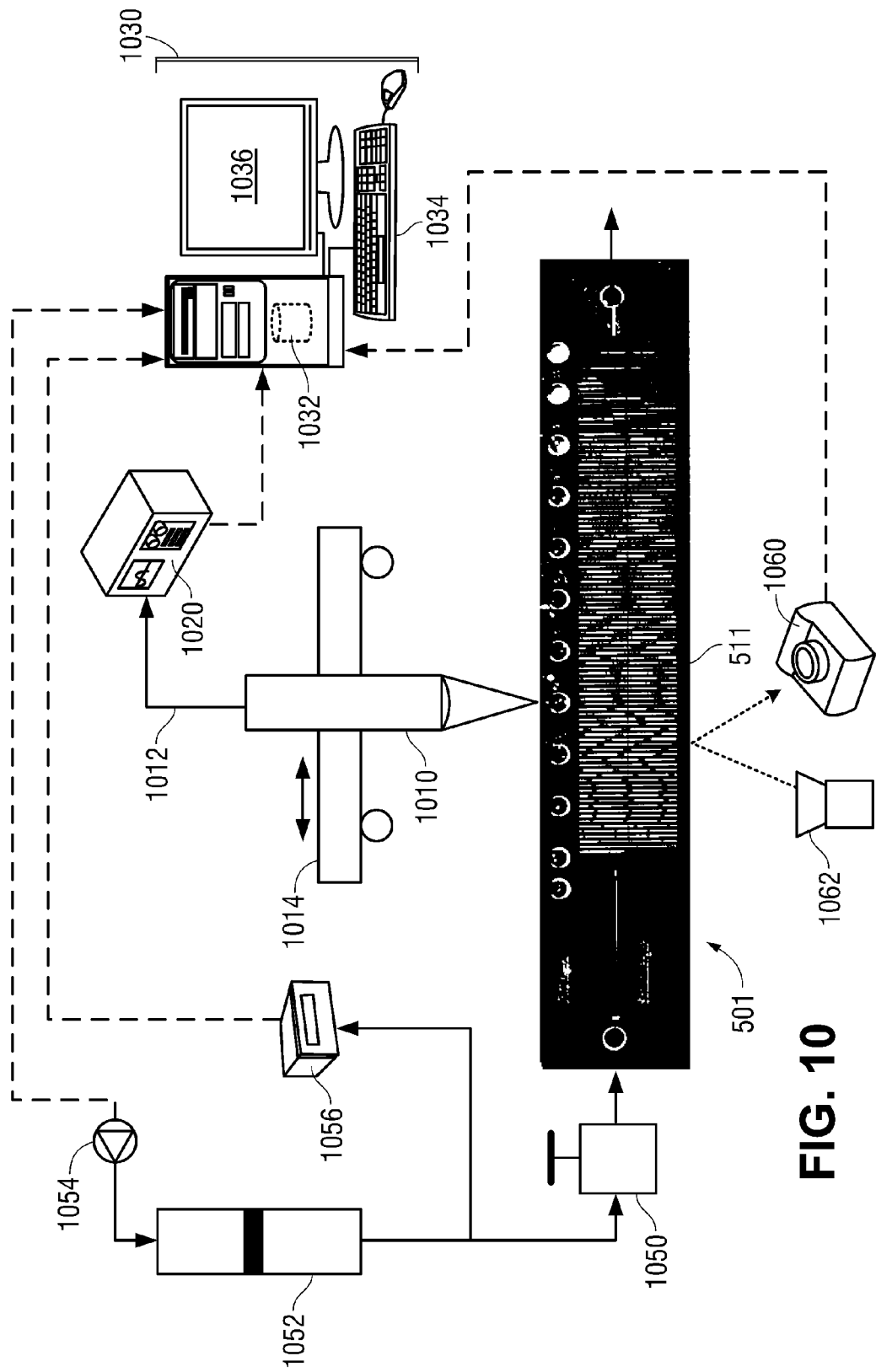
FIG. 10 is a stylized, schematic representation phase behavior analysis system, according to some embodiments.

FIG. 10 is a stylized, schematic representation phase behavior analysis system, according to some embodiments. A high capacity syringe 1054 pump electronically controlled by computer system 1030 and pushes a testing fluid stored under pressure in sample bottle 1052. The fluid is flowed from sample bottle 1052, through valve 1050 and into the serpentine channel of microfluidic device 501. A constant input pressure is maintained, and measured with a pressure gauge 1056. A strong light 1062 illuminates the transparent face 511 of the microfluidic device 501 and a camera 1060 captures videos of the flow inside the microchannel. When gas bubbles and liquid slugs are present in the same time in the channel there is a strong difference in brightness between these two phases. The images captured by the camera 1060 provide then the distribution of slugs and bubbles along the flow. The optical sensor 1010 is mounted on a high-precision stage 1014. The optical sensor 1010 moves along the back face of the microfluidic device 501 and measures the deformation of the membrane for each cavity on device 501. A spectrometer 1020 receives signals from the optical sensor 1010 via optical fiber link 1012. The results of the spectrometer are fed to the computer system 1030, thus giving a record of the pressure inside the channel at the locations of the cavities on device 501. Computer system 1030 includes a one or more processors, a storage system 1032 (which includes one or more removable storage devices that accept computer readable media), display 1036, and one or more human input devices 1034, such as a keyboard and/or a mouse. Computer system 1030 also includes a data acquisition system for collecting data from the spectrometer 1020.

The videos from camera 1060 are stored on computer system 1030 using a video acquisition program, such as is available from EPIX, Inc. of USA. According to some embodiments, a video of the full image of the microchannel is made of approximately 300 frames. According to some embodiments, the controller of pump 1054, the pressure gauge 1056, the stage 1014 and the optical sensor 1012 are all in communication with a control application on computer system 1030 such as the LabVIEW program from National Instruments Corporation, which controls all the devices and records the measurements.

Figure 11:
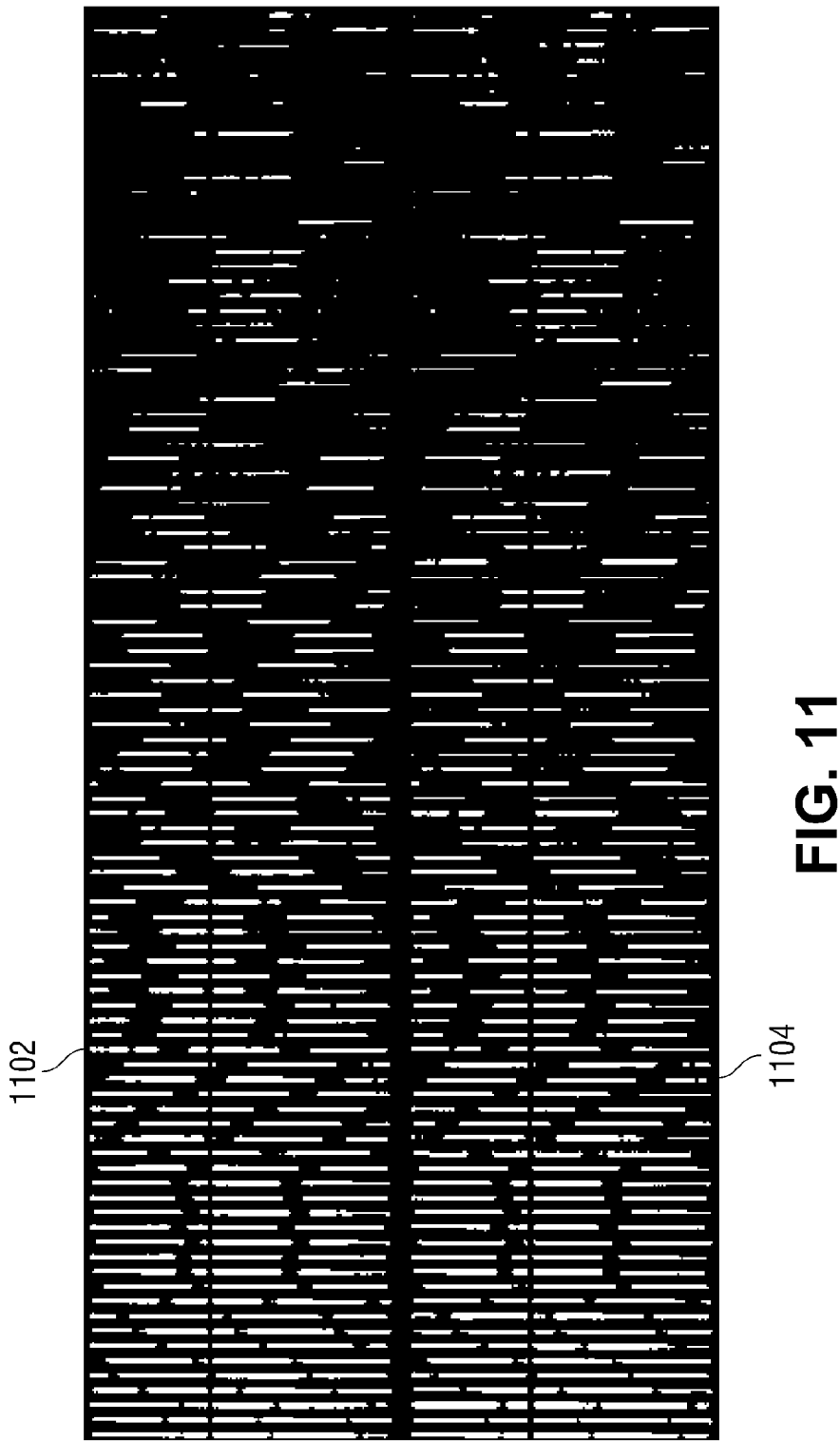
FIG. 11 shows an example of a frame of captured video from a fluid flowing through a microfluidic device, according to some embodiments.

FIG. 11 shows an example of a frame of captured video from a fluid flowing through a microfluidic device, according to some embodiments. A measurement is made up of one or more videos of the flow plus the measured pressure values at the different cavities of the microfluidic device using the optical sensor. Frame 1102 is a frame from a captured video of the flow, while frame 1104 is an image resulting from its transformation into a binary, or black and white image. As used herein the terms "binary image" or "bi-level image" means a digital image that has only two possible values for each pixel. At the first segments (near the left side of the frames), just after the input, the pressure is still high and not much gas has gotten out of the liquid. However, further downstream (to the right side of the frames), as the pressure decreases, more and more gas gets out of the liquid.

An image processing routine running on computer system 1030, for example, programmed under Matlab, transforms the original grayscale images such as 1102 into binary images such as 1104. The process involves the sensible choice of some image processing parameters. The binary image itself is then analyzed by a computation routine, for example also programmed under Matlab. The output of the computation is the liquid fraction in each of the segments composing the microchannel. This liquid fraction is then averaged on all the frames of the captured video, thus giving a more precise measurement and a value of the standard deviation. This process thus provides the evolution of the liquid fraction along the channel.

Figure 12A:
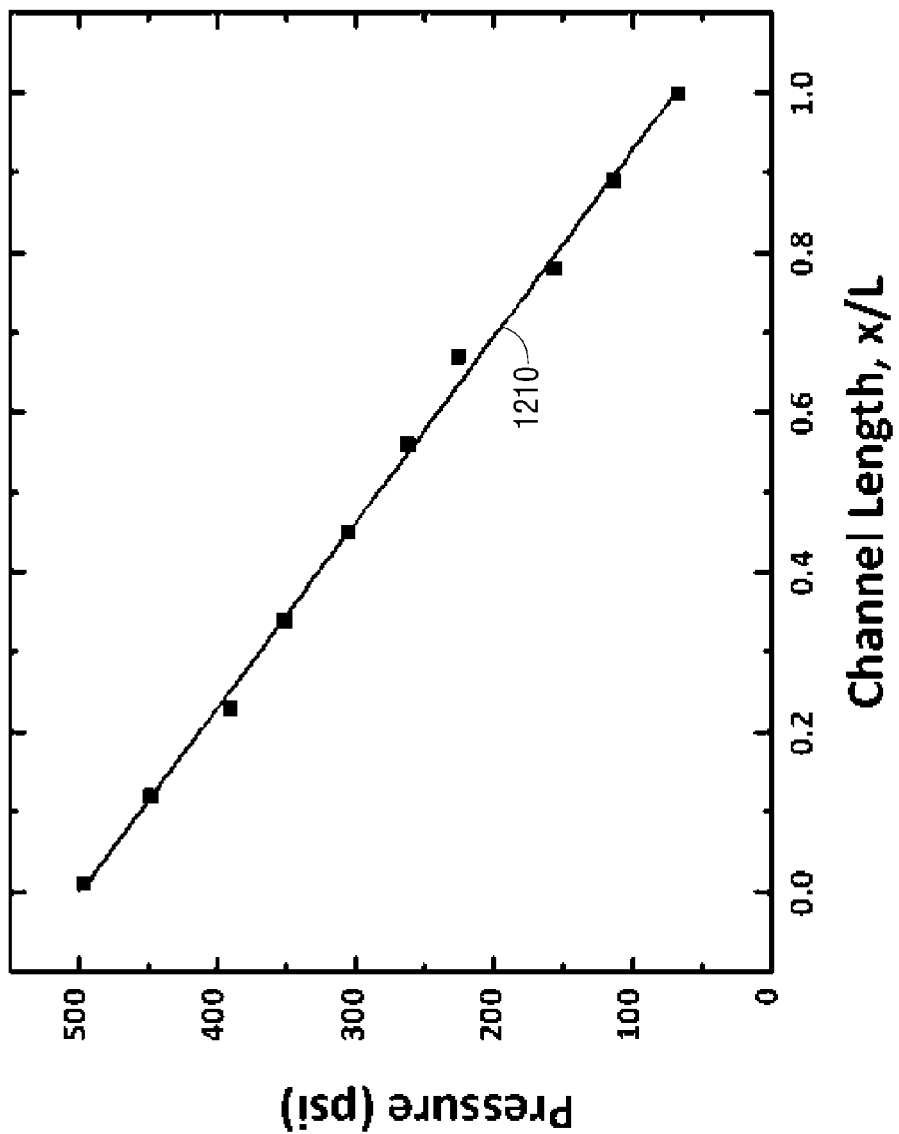
FIG. 12A is a plot showing pressure drop in a microchannel versus channel length for a mixture of $C_1$ and $C_{10}$, according to some embodiments.

FIG. 12A is a plot showing pressure drop in a microchannel versus channel length for $C_1$ and $C_{10}$, according to some embodiments. FIG. 12B is a plot showing phase volume distribution versus pressure for a mixture of $C_1$ and $C_{10}$, according to some embodiments. FIGS. 12A and 12B depict results of the measurements conducted on a live fluid in the microfluidic device shown in FIG. 5 and the setup shown in FIG. 10. The fluid is a mixture of methane and decane saturated at 500 psig. The pressure measurements of curve 1210 show a linear pressure drop inside the device. Combining the pressure measurements with phase volume distribution inside the channel provides the phase volume distribution of the fluid at different pressures as shown in FIG. 12B. In FIG. 12B, the round circles, such as point 1212, depict the measurements using the microfluidic device in the setup shown in FIG. 10, while the solid squares, such as point 1214, show the measurements conducted by a conventional PVT apparatus.

Figure 13A:
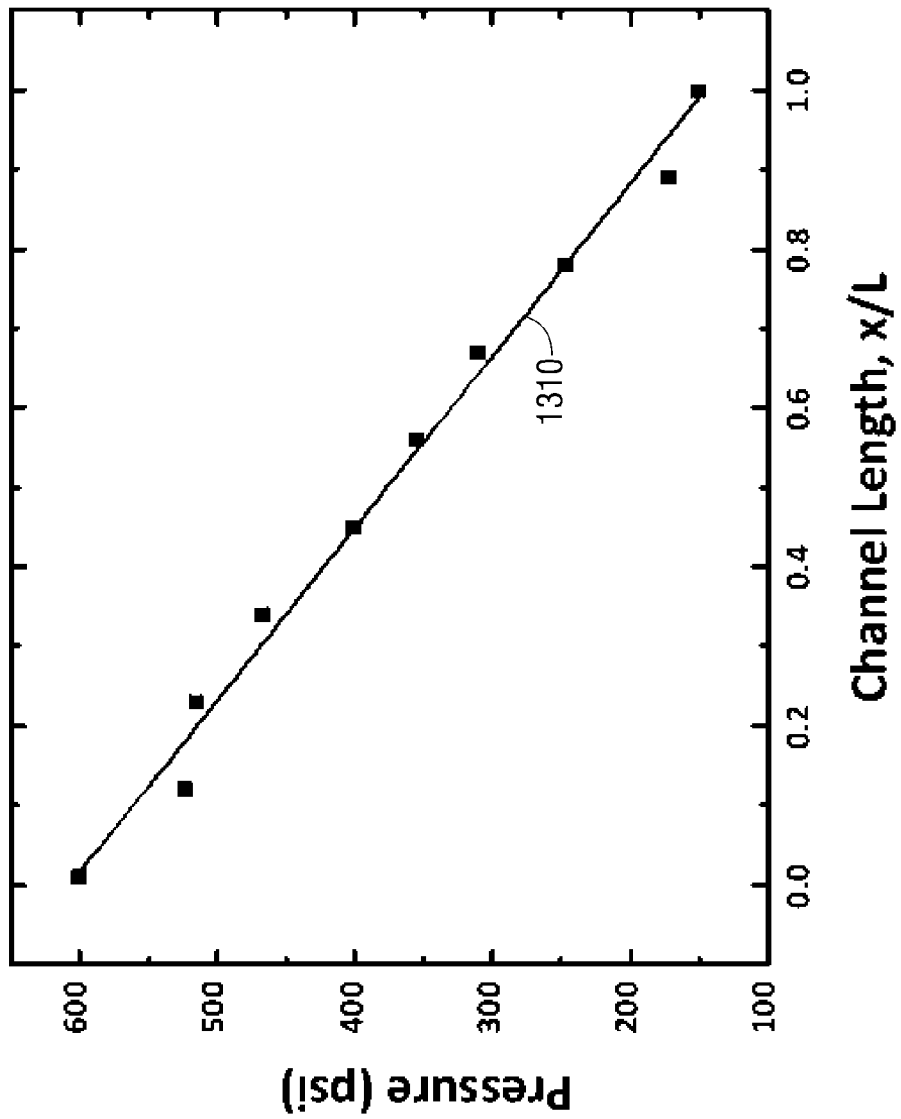
FIG. 13A is a plot showing pressure drop in a microchannel versus channel length for a mixture of a multicomponent gas and $C_{10}$, according to some embodiments.

FIG. 13A is a plot showing pressure drop in a microchannel versus channel length for a mixture of a multicomponent gas and $C_{10}$, according to some embodiments. FIG. 13B is a plot showing phase volume distribution versus pressure for a multicomponent gas and $C_{10}$, according to some embodiments. In FIGS. 13A and 13B, shows the results of measurements on a multicomponent gas is recombined with decane at 600 psig.

In FIG. 13A, the pressure measurements of curve 1310 show a linear pressure drop inside the device. In FIG. 13B, the round circles, such as point 1312, depict the measurements using the microfluidic device in the setup shown in FIG. 10, while the solid squares, such as point 1314, show the measurements conducted by a conventional PVT apparatus.

Figure 14A:
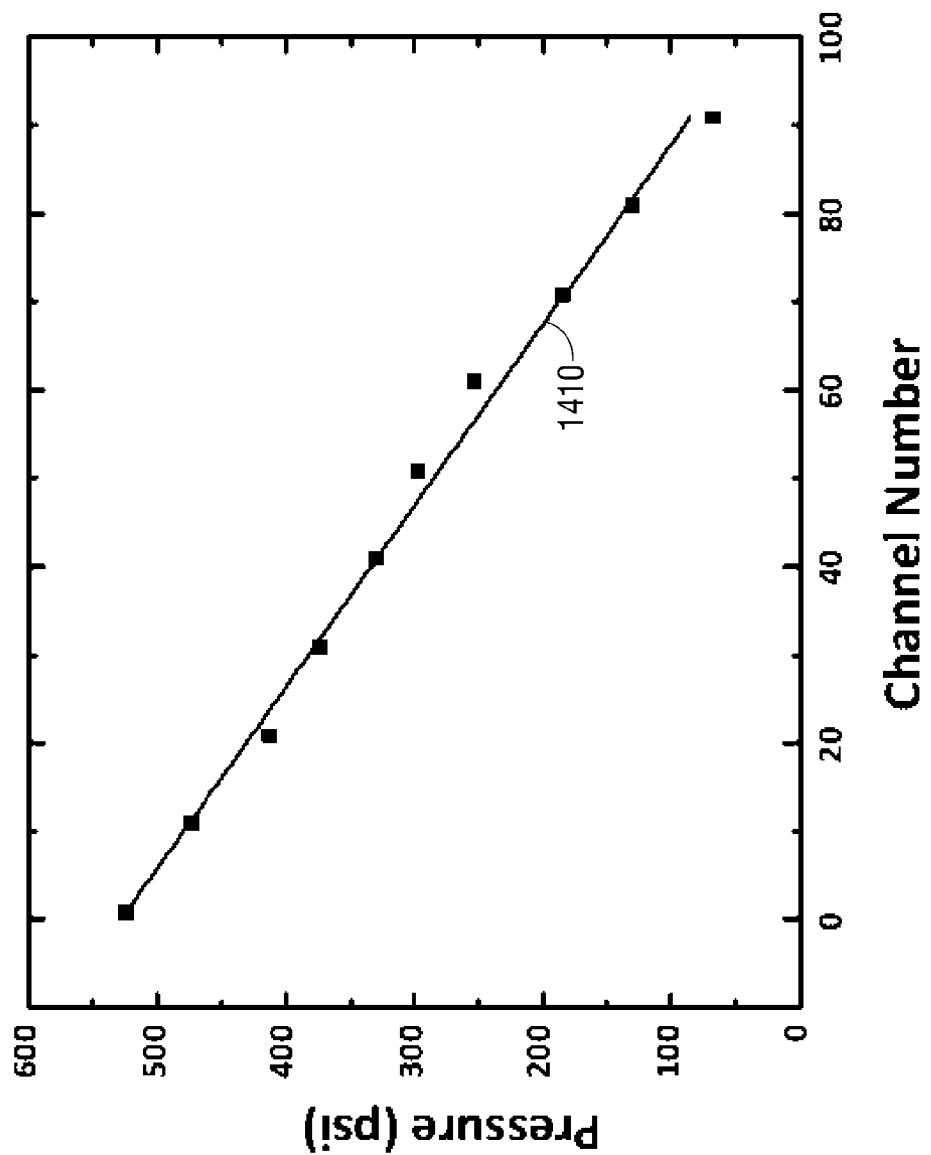
FIG. 14A is a plot showing pressure drop in a microchannel versus channel length for a mixture of a light oil and $C_1$, according to some embodiments.
Figure 14B:
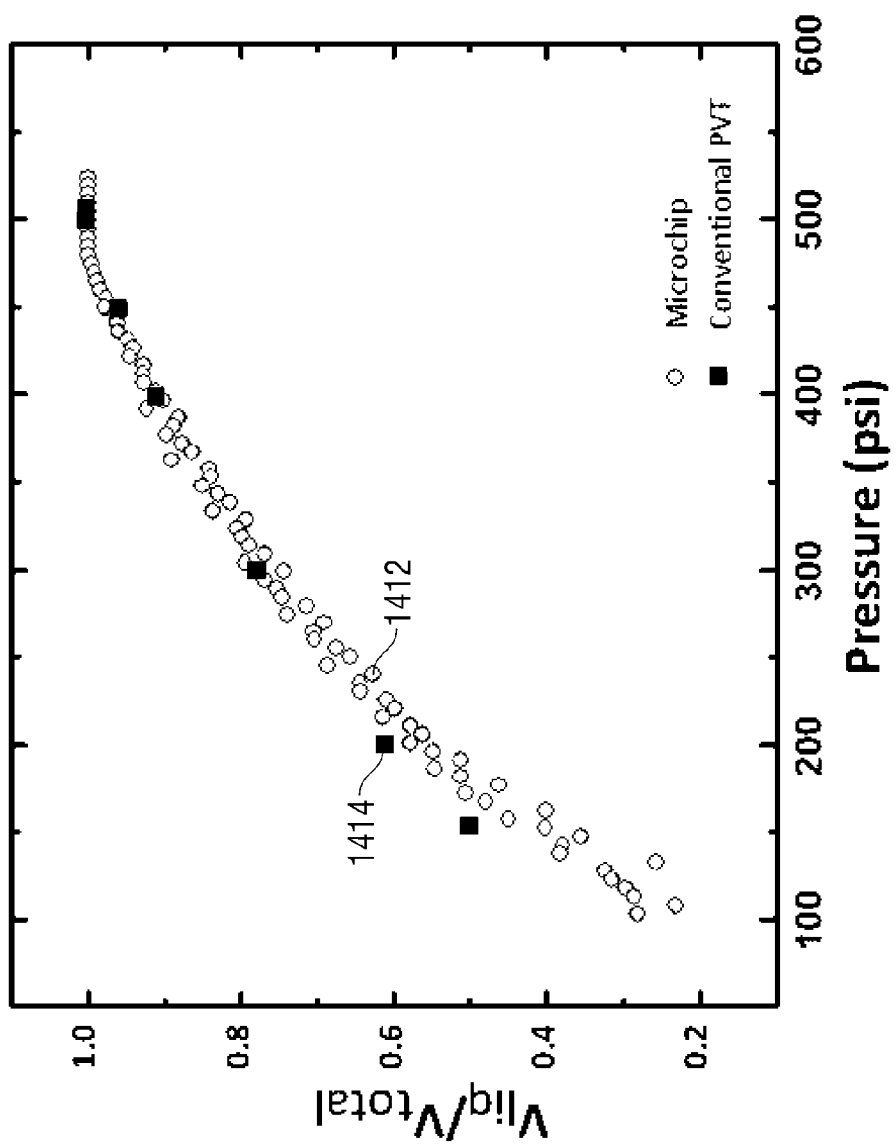
FIG. 14B is a plot showing phase volume distribution versus pressure for a mixture of a light oil and $C_1$, according to some embodiments.

FIG. 14A is a plot showing pressure drop in a microchannel versus channel length for a mixture of a light oil and $C_1$, according to some embodiments. FIG. 14B is a plot showing phase volume distribution versus pressure for a light oil and $C_1$, according to some embodiments. FIGS. 14A and 14B shows the results of measurements on a light oil recombined with methane at 500 psig saturation pressure. In FIG. 14A, the pressure measurements of curve 1410 show a linear pressure drop inside the device. In FIG. 14B, the round circles, such as point 1412, depict the measurements using the microfluidic device in the setup shown in FIG. 10, while the solid squares, such as point 1414, show the measurements conducted by a conventional PVT apparatus. As can be seen from FIGS. 12B, 13B and 14B, there is good agreement between measurements with the microfluidic device and conventional PVT.

Figure 15:
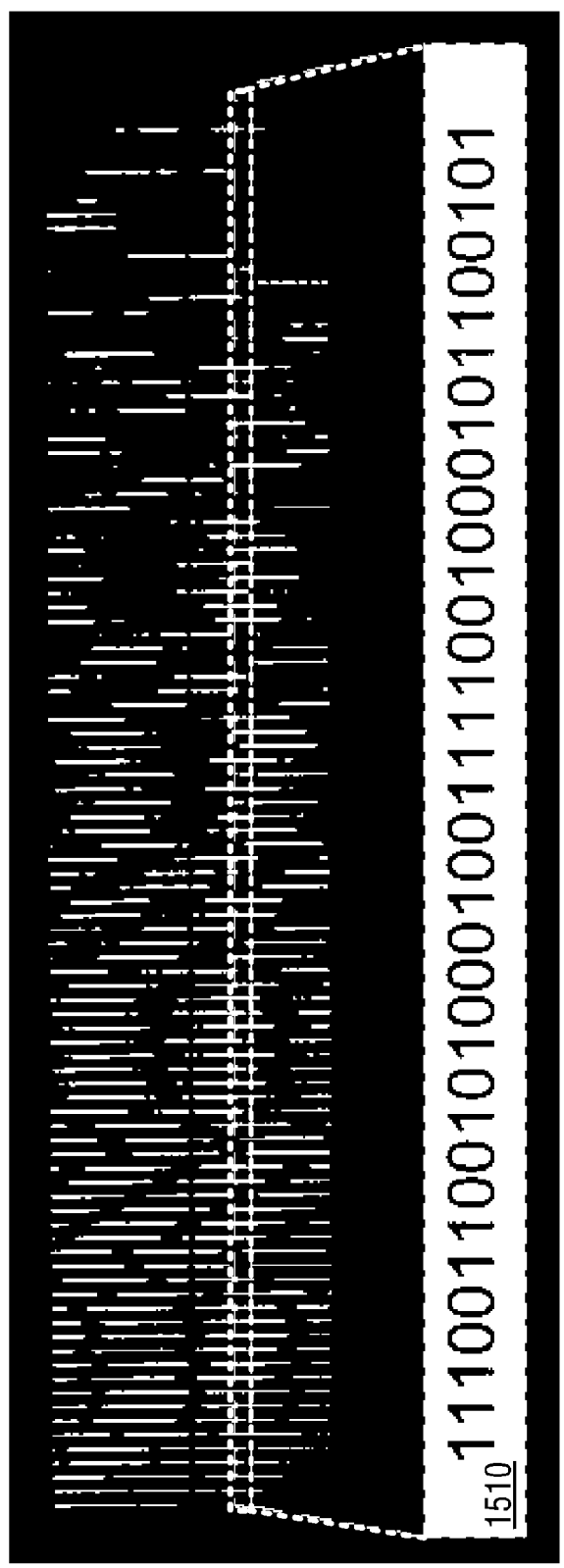
FIG. 15 shows an example of a line-scan method for measuring the liquid fraction in a microfluidic device, according to some other embodiments.

FIG. 15 shows an example of a line-scan method for measuring the liquid fraction in a microfluidic device, according to some other embodiments. The camera, such as camera 1060 of FIG. 10, can be set up to capture only a selected line in the image of the channel. In a way, the camera is working in a similar fashion as a barcode reader. Each frame, highlighted in with the dashed rectangle, is essentially a line that regroups the phase states at the same position in all the segments of the serpentine microchannel. For a given segment at the framed position is essentially a point, and the phase state can be either liquid, in which case the point corresponding to the segment in the line is bright (and is assigned a value of 1), or gas in which case the same point is dark (and is assigned a value of 0). A simplified example of the assigned values resulting from a single frame is shown as the binary string 1510.

Each measured line is at first a grayscale image then undergoes the same image processing as described above with respect to FIG. 11. A similar computation gives then the phase state (0 or 1) at the line position for each segment in the processed frame. Finally, this binary value is averaged on all the video frames to have the liquid fraction along the channel. This line-scan technique allows the capturing of approximately 20,000 frames, improving thus the averaging on the video frames and reducing the error. According to an alternative embodiment, an array of optical fibers connected an array of photo diodes is used instead of a conventional camera. Each optical fiber in the array is directed to a single vertical segment of the serpentine microchannel 505.

FIG. 16 shows an example of a matrix of phase states, according to some embodiments. The frames of the line scan video as described with respect to FIG. 15, after being converted to a binary image, can be put in a vertical sequence so as to form a matrix 1610. The obtained matrix 1610 displays the phase state in all the segments at all the instants of the video. The Y-axis is time and moves forward downward—the frame period separates two lines. The X-axis is segment number as it comes in the full image. The microchannel input is on the left, and the output is on the right. This representation constitutes a type of "fingerprint" that is specific to the flow in the channel and gives valuable information on it, as the frequency that can be observed in the matrix.

FIGS. 17A and 17B are plots showing the results of the line scan videos, according to some embodiments. The line scan technique gives liquid fraction measurements very close to those obtained with the full image video. Here again, the liquid fraction is plotted against the pressure profile in the channel and the obtained curve matches the conventional measurements one more time. In FIG. 17A, the result of line scan measurements on a methan-decane mixture saturated at 500 psig are shown in the solid squares, such as point 1710, and the conventionally measured data is shown in the open triangles, such as point 1712. In FIG. 17B the result of line scan measurements on a multicomponent gas saturated at 600 psig with decane are shown in the open circles, such as point 1720, and the conventionally measured data is shown in the solid squares such as point 1722.

Figure 18A:
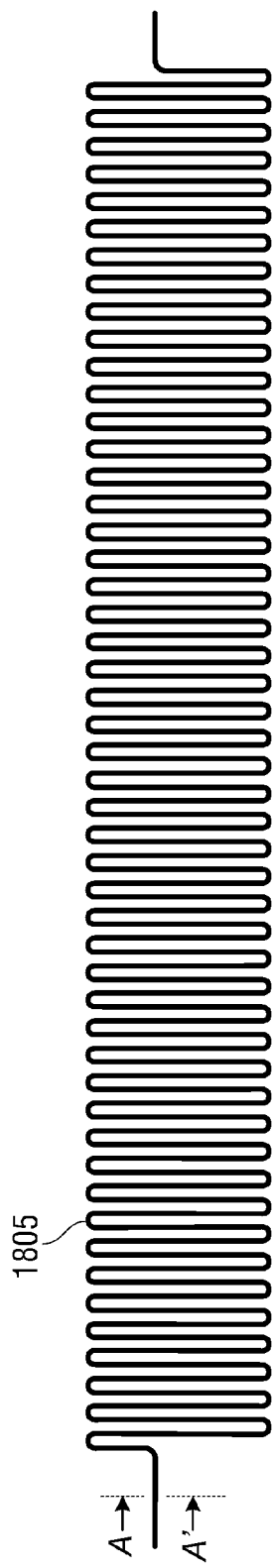
FIGS. 18A and 18B show a microchannel according to an alternative embodiment.
Figure 18B:
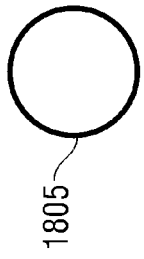
Figure 19:
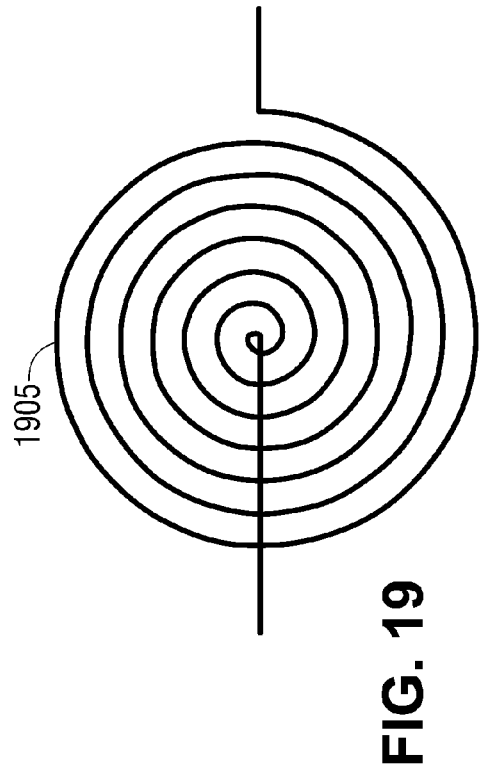
FIG. 19 shows an example of a spiral microchannel layout pattern, according to an alternative embodiment.

FIGS. 18A and 18B show a microchannel according to an alternative embodiment. Although much of the discussion herein refers to microchannels as being fabricated from a conventional silicon etching process, other types of microchannels can be used with the microfluidic devices and related techniques described herein. For example, the microchannel 1805 is made from a glass tube formed in a serpentine shape. FIG. 18B shows a cross section of the glass tube microchannel, which is round. Furthermore, layout patterns of the microchannel other than serpentine can be used the microfluidic devices. FIG. 19 shows an example of a spiral microchannel layout pattern, according to an alternative embodiment. Microchannel 1905 can be fabricated with conventional silicon processing or can be made using other techniques, for example it could be a glass tube as shown in FIGS. 18A and 18B.

Although many embodiments have been described herein with respect to analysis of reservoir fluids, the present invention is also applicable to the analysis of many other types of fluids. According to some embodiments analysis of one or more types of biomedical fluids is provided including but not limited to bodily fluids such as blood, urine, serum, mucus, and saliva. According to other embodiments analysis of one or more fluids is provided in relation to environmental monitoring, including by not limited to water purification, water quality, and waste water processing, and potable water and/or sea water processing and/or analysis. According to yet other embodiments, analysis of other fluid chemical compositions is provided.

Whereas many alterations and modifications of the present invention will no doubt become apparent to a person of ordinary skill in the art after having read the foregoing description, it is to be understood that the particular embodiments shown and described by way of illustration are in no way intended to be considered limiting. Further, the invention has been described with reference to particular preferred embodiments, but variations within the spirit and scope of the invention will occur to those skilled in the art. It is noted that the foregoing examples have been provided merely for the purpose of explanation and are in no way to be construed as limiting of the present invention. While the present invention has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A system for analyzing phase properties in a microfluidic device comprising:
   a microchannel adapted to carry a fluid and having an entrance passageway and an exit passageway;
   a fluid introduction system in fluid communication with the entrance passageway, and adapted to introduce the fluid under pressure via the entrance passageway; and
   a first optical sensing system adapted and positioned to detect phase states of the fluid at a first plurality of locations along the microchannel, wherein the first optical sensing system generates a plurality of digital images of the fluid in the microchannel and includes a processing system adapted and programmed to distinguish gas from liquid phases of the fluid in the microchannel at the first plurality of locations based on a plurality of binary images generated from the plurality of digital images, and wherein the processing system is further programmed to estimate values relating to a volume fraction of liquid or gas in the fluid for a plurality of pressures based at least in part on the plurality of binary images.

2. A system according to claim 1, wherein the plurality of digital images are created using an array of optical fibers directed towards portions of the microchannel.

3. A system according to claim 1, further comprising a pressure measurement system adapted and positioned to measure pressure of the fluid at a second plurality of locations along the microchannel.

4. A system according to claim 3, wherein the pressure measurement system comprises:
   one or more deformable membranes adapted and positioned so as to deform under fluid pressure in the microchannel; and
   a second optical sensing system adapted and positioned to detect deformation of the one or more deformable membranes.

5. A system according to claim 1, wherein the fluid is of a type selected from the group consisting of: reservoir fluid, biomedical fluid, and a fluid being monitored in connection with environmental monitoring.

6. A system according to claim 1, further comprising a processing system adapted and programmed to estimate bubble point pressures for the fluid based at least in part on the detected phase states of the fluid.

7. A system according to claim 1, further comprising a processing system adapted and programmed to estimate a relationship for phase behavior versus pressure for the fluid based at least in part on the detected phase states of the fluid.

8. A system according to claim 1, further comprising a processing system adapted and programmed to estimate a phase volume distribution ratio for the fluid based at least in part on the detected phase states of the fluid.

9. A system according to claim 1, wherein the microchannel has a substantially rectangular cross section.

10. A system according to claim 1, wherein the microchannel is defined at least in part by a channel etched into a silicon substrate and a transparent glass substrate so as to allow the first optical sensing system to generate the plurality of digital images of the fluid in the microchannel.

11. A system according to claim 1, wherein the microchannel exhibits a serpentine shape and a length of at least one meter.

12. A system according to claim 1, wherein the microchannel exhibits a width within a range of two micrometers to hundreds of micrometers.

13. A method for analyzing phase properties in a microfluidic device comprising:
   providing a microchannel adapted to carry a fluid, having an entrance passageway and an exit passageway:
   introducing fluid under pressure into the microchannel via the entrance passageway; and
   optically sensing phase states of the fluid at a first plurality of locations along the microchannel, wherein optically sensing comprises generating a plurality of digital images of the fluid in the microchannel, generating a plurality of binary images based on the plurality of digital images, and distinguishing gas phase of the fluid from liquid phase of the fluid in the microchannel at the first plurality of locations based on the plurality of binary images, and wherein optically sensing further comprises estimating values relating to a volume fraction of liquid or gas in the fluid for a plurality of pressures based at least in part on the plurality binary images.

14. A method according to claim 13, further comprising measuring pressure of the fluid at a second plurality of locations along the microchannel.

15. A method according to claim 14 wherein the pressure is measured by optically sensing deformation of one or more deformable membranes that are positioned so as to deform under fluid pressure in the microchannel.

16. A method according to claim 13 wherein the fluid is of a type selected from the group consisting of: reservoir fluid, biomedical fluid, and a fluid being monitored in connection with environmental monitoring.

17. A method according to claim 13 further comprising estimating bubble point pressures for the fluid based at least in part on the detected phase states of the fluid.

18. A method according to claim 13 further comprising estimating a relationship for phase behavior versus pressure for the fluid based at least in part on the detected phase states of the fluid.

19. A method according to claim 13 further comprising estimating a phase volume distribution ratio for the fluid based at least in part on the detected phase states of the fluid.

20. A method according to claim 13, wherein the microchannel has a substantially rectangular cross section.

21. A method according to claim 13, wherein the microchannel is defined at least in part by a channel etched into a silicon substrate and a transparent glass substrate so as to allow the optical sensing system to generate a plurality of digital images of the fluid in the microchannel.

22. A method according to claim 13, wherein the microchannel exhibits a serpentine shape and a length of at least one meter.

23. A method according to claim 13, wherein the microchannel exhibits a width within a range of two micrometers to hundreds of micrometers.

* * * * *